United States Patent
Atis

(10) Patent No.: US 8,323,628 B2
(45) Date of Patent: Dec. 4, 2012

(54) LONG WEAR COSMETIC COMPOSITION

(75) Inventor: Balanda Atis, Newark, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/019,435

(22) Filed: Feb. 2, 2011

(65) Prior Publication Data

US 2011/0123472 A1 May 26, 2011

Related U.S. Application Data

(63) Continuation of application No. 10/542,452, filed as application No. PCT/US2004/001071 on Jan. 16, 2004, now abandoned.

(60) Provisional application No. 60/440,626, filed on Jan. 17, 2003.

(51) Int. Cl.
*A61Q 1/10* (2006.01)
*A61Q 1/04* (2006.01)
*A61Q 5/00* (2006.01)
*A61Q 19/00* (2006.01)

(52) U.S. Cl. ..... 424/70.7; 424/64; 424/70.1; 424/70.12; 424/70.17; 424/401

(58) Field of Classification Search ............... None
See application file for complete search history.

(56) References Cited

U.S. PATENT DOCUMENTS

| | | | |
|---|---|---|---|
| 3,148,125 A | 9/1964 | Strianse et al. | |
| 3,578,719 A | 5/1971 | Kalopissis et al. | |
| 3,645,705 A | 2/1972 | Miller et al. | |
| 3,666,671 A | 5/1972 | Kalopissis et al. | |
| 3,877,955 A | 4/1975 | Kalopissis et al. | |
| 3,928,224 A | 12/1975 | Vanlerberghe et al. | |
| 4,087,466 A | 5/1978 | Vanlerberghe et al. | |
| 4,307,079 A | 12/1981 | Zorayan et al. | |
| 4,311,695 A | 1/1982 | Starch | |
| 5,015,469 A | 5/1991 | Yoneyama et al. | |
| 5,330,747 A | 7/1994 | Krzysik | |
| 5,500,209 A | 3/1996 | Ross et al. | |
| 5,589,165 A | 12/1996 | Yoshida et al. | |
| 5,614,200 A * | 3/1997 | Bartholomey et al. | 424/401 |
| 5,654,362 A | 8/1997 | Schulz, Jr. et al. | |
| 5,676,938 A | 10/1997 | Kimura et al. | |
| 5,783,657 A | 7/1998 | Pavlin et al. | |
| 5,849,275 A | 12/1998 | Calello et al. | |
| 5,945,095 A | 8/1999 | Mougin et al. | |
| 5,959,009 A | 9/1999 | Konik et al. | |
| 5,998,570 A | 12/1999 | Pavlin et al. | |
| 6,132,745 A | 10/2000 | Marchi-Lemann et al. | |
| 6,251,375 B1 | 6/2001 | Bara | |
| 6,423,306 B2 | 7/2002 | Caes et al. | |
| 6,479,040 B1 | 11/2002 | Barone et al. | |
| 6,589,517 B1 | 7/2003 | McKelvey et al. | |
| 2002/0028223 A1 | 3/2002 | Vatter et al. | |
| 2002/0031488 A1 | 3/2002 | Kanji et al. | |
| 2002/0114773 A1 | 8/2002 | Kanji et al. | |
| 2003/0039620 A1 | 2/2003 | Rodriguez et al. | |
| 2003/0049217 A1 | 3/2003 | Rodriguez et al. | |

FOREIGN PATENT DOCUMENTS

| | | |
|---|---|---|
| EP | 0 179 416 A2 | 4/1986 |
| FR | 1 477 048 | 4/1967 |
| FR | 2 091 516 | 1/1972 |
| FR | 2 328 763 | 5/1977 |
| JP | A S61-100513 | 5/1986 |
| JP | A H03-141212 | 6/1991 |
| JP | A S61-210019 | 9/1996 |
| JP | A H11-049657 | 2/1999 |
| JP | A 2001-072537 | 3/2001 |
| JP | 2002-234819 | 8/2002 |
| WO | WO 98/42298 | 10/1998 |

OTHER PUBLICATIONS

International Search Report dated Sep. 3, 2004, for PCT/US04/01071.
"The Journal of the Society of Cosmetic Chemists", Mar. 1954, (vol. 5) pp. 249-256.
Kirk-Othmer, "Encyclopedia of Chemical Technology Third Edition", vol. 22, pp. 347-377, 1983.
"Microemulsions Theory and Practice", L.M. Prince, Ed., Academic Press (1977), vol. 2 pp. 21-32.
International Cosmetic Ingredient Dictionary and Handbook, Seventh Ed., (1997) vol. 2 pp. 1654-1655.
International Cosmetic Ingredient Dictionary and Handbook, Seventh Ed., (1997) vol. 2 pp. 1656-1661.

* cited by examiner

*Primary Examiner* — Jyothsna Venkat
(74) *Attorney, Agent, or Firm* — O'Brien Jones, PLLC

(57) ABSTRACT

The present invention relates to long-wearing, non-aqueous based cosmetic compositions, and related dermatological, pharmaceutical or hygiene compositions. The present invention provides a non-aqueous based composition comprising one or a mixture of two or more emulsifiers.

11 Claims, No Drawings

LONG WEAR COSMETIC COMPOSITION

REFERENCE TO PRIOR APPLICATIONS

This is a continuation of application Ser. No. 10/542,452, filed May 23, 2006 now abandoned, which is a national stage filing under 35 U.S.C. §371 of PCT/US04/01071 filed on Jan. 16, 2004, and claims the benefit of U.S. Provisional Application No. 60/440,626, filed Jan. 17, 2003, all of which are incorporated herein by reference.

FIELD OF THE INVENTION

The present invention relates to long-wearing, non-aqueous cosmetic compositions, and related dermatological, pharmaceutical and hygiene compositions.

BACKGROUND OF THE INVENTION

Non-aqueous cosmetic compositions, such as, mascara, are generally well-known. There are several properties of such compositions that are desirable for the wearer, such as, long-wear, resistance to water exposure, smooth consistency, glossiness and overall satisfactory appearance. Accordingly, there is a need in the cosmetic art to provide cosmetic compositions that exhibit these properties.

Emulsifiers useful in cosmetic compositions are generally well-known. As the name suggests, emulsifiers are used to facilitate the emulsion of oil and water phases in various compositions.

SUMMARY OF THE INVENTION

The present inventors have discovered that the wear or duration of a cosmetic composition, such as, mascara, can be significantly improved by the presence of one or more emulsifiers.

"Long-wear," "Improved wear" and similar terminology means the ability of the non-aqueous composition to stay on the applied surface for long periods of time. As used in the present invention, the terms refer to the ability of the present compositions to stay on the surface for long periods, relative to similar compositions that do not contain an emulsifier.

The term non-aqueous, as used herein in reference to the invention, includes compositions that contain water and/or at least one water-soluble solvent, in a total content lesser or equal to 20% by weight of the composition. In preferred embodiments of the invention, the compositions do not contain water, or contain 1, 2, 3, 4, 5, 6, 7, 8, 9, 10, 11, 12, 13, 14, 15, 16, 17, 18, 19 or 20% water. In further preferred embodiments of the invention, the compositions do not contain water-soluble solvents, or contain 1, 2, 3, 4, 5, 6, 7, 8, 9, 10, 11, 12, 13, 14, 15, 16, 17, 18, 19 or 20% water-soluble solvents.

The term "water-soluble solvent" may be defined as a compound liquid at room temperature and miscible in water (miscibility in water is greater than 50% in weight at 25° C. and atmospheric pressure). Preferred water-soluble solvents which may be used in the compositions according to the invention are usually volatile solvents. Lower mono-alcohols having from 1 to 5 carbon atoms such as ethanol and isopropanol, glycols having from 2 to 8 carbon atoms such as ethylene glycol, propylene glycol, 1,3-butylene glycol and dipropylene glycol, $C_3$ and $C_4$ ketones and $C_2$ to $C_4$ aldehydes may be cited amongst the preferable water-soluble solvents which can be used in the compositions according to the invention.

Water and/or water-soluble solvent(s) may be used as such in the formulation according to the invention or they may be used with one or several ingredients constituting said composition. Thus water can also be inserted in the composition with the use of latex or pseudolatex, i.e. with an aqueous dispersion of particles of polymers.

The presence of water and/or of water-soluble solvent(s) in said compositions can be advantageous in order to increase the adhesion of the composition on eyelashes or other keratinous tissues. Indeed, the higher the quantity of the non aqueous solvent is, notably volatile oil, the more slippery the application on the eyelashes is, due to the mainly "oily" nature of the composition. The partial substitution of the non-aqueous solvent with a water-soluble solvent can reduce this effect and thus increase the adhesion on eyelashes. The make-up obtained can thus be thicker.

In a highly preferred embodiment of the invention, the water and/or in water-soluble solvent(s) content can be greater or equal to 0.5%, particularly range from 1 to 18%, and more particularly from 2 to 15% by weight of the composition.

Non-aqueous compositions which can benefit from the addition of emulsifier and be converted to long-wear compositions thereby are generally any non-aqueous composition prepared or known in the field under consideration, such as the cosmetic industry. In one preferred embodiment, the non-aqueous cosmetic composition is mascara. Examples of compositions which can benefit from the addition of the emulsifier are described in U.S. Pat. Nos. 5,945,095; 5,959,009; 6,251,375; and 6,423,306, the contents of which are incorporated herein by reference.

The invention emulsifiers are not limited, and include those listed, for example, in the International Cosmetic Ingredient Dictionary and Handbook, 9th Ed (2002), the contents of which are incorporated herein by reference. Preferred examples of emulsifiers useful herein include polysorbate 20 (Tween 20), glyceryl stearate, stearic acid, and/or sodium dihydroxycetyl phosphate. When using stearic acid it is preferred to combine it with triethanolamine (TEA). Of course, one or a mixture of two or more emulsifiers may be present in the non-aqueous make-up compositions according to the invention.

Other preferred emulsifiers include those having at 25° C. an HLB (hydrophilic-lipophilic balance), in the Griffin sense, of greater than or equal to 8 is used. The HLB value according to Griffin is defined in J. Soc. Cosm. Chem. 1954 (volume 5), pages 249-256.

The compositions according to the invention may especially contain emulsifying surfactants present especially in a proportion ranging from 0.1% to 40% and better still from 0.5% to 20% by weight relative to the total weight of the composition.

These surfactants may be chosen from nonionic, anionic, cationic and amphoteric surfactants or emulsifying surfactants. Reference may be made to the document "Encyclopedia of Chemical Technology, Kirk-Othmer", volume 22, p. 333-432, 3rd edition, 1979, Wiley, for the definition of the properties and (emulsifying) functions of surfactants, in particular pp. 347-377 of this reference, for anionic, amphoteric and nonionic surfactants.

A preferred emulsifier system comprises at least one ionic surfactant and at least one nonionic surfactant with an HLB of greater than or equal to 8 at 25° C., optionally combined with at least one gelling polymer.

As non-limiting illustrations of nonionic surfactants with an HLB of greater than or equal to 8 at 25° C. which may be used, alone or as a mixture, in the compositions according to the invention, mention may be made especially of:

oxyethylenated and/or oxypropylenated ethers (which may comprise from 1 to 150 oxyethylene and/or oxypropylene groups) of glycerol;

oxyethylenated and/or oxypropylenated ethers (which may comprise from 1 to 150 oxyethylene and/or oxypropylene groups) of fatty alcohols (especially of C8-C24 and preferably C12-C18 alcohol), such as oxyethylenated cetearyl alcohol ether containing 30 oxyethylene groups (CTFA name "Ceteareth-30") and the oxyethylenated ether of the mixture of C12-C15 fatty alcohols comprising 7 oxyethylene groups (CTFA name "C12-15 Pareth-7" sold under the name "Neodol 25-7®" by Shell Chemicals);

fatty acid esters (especially of a C8-C24 and preferably C16-C22 acid) of polyethylene glycol (which may comprise from 1 to 150 ethylene glycol units), such as PEG-50 stearate and PEG-40 monostearate sold under the name Myrj 52P by the company ICI Uniqema;

fatty acid esters (especially of a C8-C24 and preferably C16-C22 acid) of oxyethylenated and/or oxypropylenated glyceryl ethers (which may comprise from 1 to 150 oxyethylene and/or oxypropylene groups), for instance PEG-200 glyceryl monostearate sold under the name "Simulsol 220 ™" by the company SEPPIC; glyceryl stearate polyethoxylated with 30 ethylene oxide groups, for instance the product Tagat S sold by the company Goldschmidt, glyceryl oleate polyethoxylated with 30 ethylene oxide groups, for instance the product Tagat O sold by the company Goldschmidt, glyceryl cocoate polyethoxylated with 30 ethylene oxide groups, for instance the product Varionic LI 13 sold by the company Sherex, glyceryl isostearate polyethoxylated with 30 ethylene oxide groups, for instance the product Tagat L sold by the company Goldschmidt, and glyceryl laurate polyethoxylated with 30 ethylene oxide groups, for instance the product Tagat I from the company Goldschmidt;

fatty acid esters (especially of a C8-C24 and preferably C16-C22 acid) of oxyethylenated and/or oxypropylenated sorbitol ethers (which may comprise from 1 to 150 oxyethylene and/or oxypropylene groups), for instance polysorbate 60 sold under the name "Tween 60" by the company Uniqema;

dimethicone copolyol, such as the product sold under the name "Q2-5220" by the company Dow Corning;

dimethicone copolyol benzoate (Finsolv SLB 101 and 201 by the company Finetex);

copolymers of propylene oxide and of ethylene oxide, also known as BO/PO polycondensates;

and mixtures thereof.

The BO/PO polycondensates are more particularly copolymers consisting of polyethylene glycol and polypropylene glycol blocks, for instance polyethylene glycol/polypropylene glycol/polyethylene glycol triblock polycondensates. These triblock polycondensates have, for example, the following chemical structure:

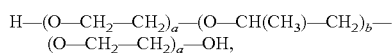

in which a ranges from 2 to 120 and b ranges from 1 to 100.

The BO/PO polycondensate preferably has a weight-average molecular weight ranging from 1 000 to 15 000 and better still ranging from 2 000 to 13 000. Advantageously, the said BO/PO polycondensate has a cloud point, at 10 g/l in distilled water, of greater than or equal to 20° C. and preferably greater than or equal to 60° C. The cloud point is measured according to ISO standard 1065. As BO/PO polycondensates that may be used according to the invention, mention may be made of the polyethylene glycol/polypropylene glycol/polyethylene glycol triblock polycondensates sold under the name "Synperonic", for instance "Synperonic PE/L44" and "Synperonic PE/F127", by the company ICI, and mixtures thereof.

One or more nonionic surfactants with an HLB of less than 8 at 25° C. may be combined with this nonionic surfactant with an HLB of greater than or equal to 8.

As non-limiting illustrations of these agents with an HLB of less than 8 at 25° C., mention may be made more particularly of:

saccharide esters and ethers, such as sucrose stearate, sucrose cocoate and sorbitan stearate, and mixtures thereof, for instance Arlatone 2121 sold by the company ICI;

fatty acid esters (especially of a C8-C24 and preferably C16-C22 acid) of polyols, especially of glycerol or of sorbitol, such as glyceryl stearate, glyceryl stearate such as the product sold under the name Tegin M by the company Goldschmidt, glyceryl laurate such as the product sold under the name Imwitor 312 by the company Hills, polyglyceryl-2 stearate, sorbitan tristearate or glyceryl ricinoleate;

the mixture of cyclomethicone/dimethicone copolyol sold under the name "Q2-3225C" by the company Dow Corning.

The amount of nonionic surfactant is generally adjusted so as to obtain a composition having the parameters as defined above. The determination of this amount falls within the competence of a person skilled in the art.

As non-limiting illustration of the scope of the invention, this amount of nonionic surfactant with an HLB of greater than or equal to 8 may range from 0.01% to 40% by weight, in particular from 0.1% to 25% be weight or even from 0.5% to 15% by weight and better still from 0.5% to 10% by weight, relative to the total weight of the composition.

The ionic surfactants used in the context of the present invention may be anionic or cationic. However, the choice of at least one anionic surfactant is generally favoured.

As illustrations of anionic surfactants that are suitable for the invention, mention may be made more particularly of:

$C_{16}$-$C_{30}$ fatty acid salts, especially those derived from amines, for instance triethanolamine stearate;

polyoxyethylenated fatty acid salts, especially those derived from amines or alkali metal salts, and mixtures thereof;

phosphoric esters and salts thereof, such as "DEA oleth-10 phosphate" (Crodafos N 10N from the company Croda);

sulphosuccinates such as "Disodium PEG-5 citrate lauryl sulphosuccinate" and "Disodium ricinoleamido MEA sulphosuccinate";

alkyl ether sulphates, such as sodium lauryl ether sulphate;

isethionates;

acylglutamates such as "Disodium hydrogenated tallow glutamate" (Amisoft HS-21 R sold by the company Ajinomoto), and mixtures thereof.

Triethanolamine stearate is most particularly suitable for the invention. This surfactant is generally obtained by simple mixing of stearic acid and triethanolamine Illustrations of cationic surfactants that may especially be mentioned include:

alkylimidazolidiniums, such as isostearylethylimidonium ethosulphate, ammonium salts, such as N,N,N-trimethyl-1-docosanaminium chloride (behentrimonium chloride).

The compositions according to the invention may also contain one or more amphoteric surfactants, for instance N-acylamino acids such as N-alkylaminoacetates and disodium cocoamphodiacetate, and amine oxides such as stearamine oxide, or alternatively silicone surfactants, for instance dimethicone copolyol phosphates such as the product sold under the name "Pecosil PS 100" by the company Phoenix Chemical.

In general, the compositions according to the invention may contain from 0.01% to 30% by weight, in particular from 0.1% to 15% by weight or even from 0.5% to 10% by weight of ionic surfactant, relative to the total weight of the composition.

Methods of preparing non-aqueous compositions are within the skill of one of ordinary skill in the art. See, for example, U.S. Pat. Nos. 5,945,095; 5,959,009; 6,251,375; and 6,423,306, the contents of which are incorporated herein by reference.

The non-aqueous compositions of the invention may also contain other suitable ingredients generally employed in cosmetic or topical compositions. Such additives include, but are not limited to, film formers, waxes, oils, thickening agents, dispersing agents, suspending agents, plasticizing agents, solvents, colorants, fillers, emollients, preserving agents, conditioning agents, antioxidants, vitamins, vitamin derivatives, water proofing additives, fragrances and botanical extracts.

The invention compositions can be used for making-up the eyes, hair, lips, and/or skin, by applying the compositions of the present invention to the appropriate surface. Mascara employing the composition of the invention preferably produces increased stability and better adherence to keratin fibres, and provides greater wear resistance, improved water resistance, and improved cosmetic properties. Lotions employing the composition of the invention preferably provide increased transfer resistance and water resistance and greater wearability. Eyeliner employing the composition of the invention preferably produces increased stability and better adherence to eyelid tissue, and may also provide greater water resistance and improved cosmetic properties.

Accordingly, one object of the present invention is to provide a non-aqueous based composition comprising one or a mixture of two or more emulsifiers. Preferably, the emulsifier(s) are present in an amount suitable for imparting a long-wear property to the composition. In a preferred embodiment, the emulsifier(s) are selected from fatty acids, salts of phosphate esters of alcohols, glyceryl esters, ethoxylated surfactants, or mixtures thereof. In another embodiment, the emulsifier(s) are selected from stearic acid, sodium dihydroxycetyl phosphate, glyceryl stearate, polysorbate 20, or mixtures thereof. In another preferred embodiment, the composition is a mascara composition.

Another object of the present invention is to provide a method of preparing a long-wearing cosmetic composition, comprising adding one or more emulsifiers to a non-aqueous medium. Preferably, the emulsifier(s) are added in an amount suitable for imparting a long-wear property to the composition.

Another object of the present invention is to provide a method of making-up the eyes, hair, lips, and/or skin with the compositions of the present invention by applying the invention composition to the appropriate surface.

DETAILED DESCRIPTION OF THE INVENTION

The present invention provides a non-aqueous based composition comprising one or more emulsifiers. Preferably, the emulsifier(s) are present in an amount suitable for imparting a long-wear property to the composition.

Preferably, the emulsifiers are anionic, nonionic, amphoteric and/or zwitterionic surfactants.

In a preferred embodiment the surfactants are characterized by fatty acids, salts of phosphate esters of alcohols, glyceryl esters, ethoxylated surfactants, or mixtures thereof. In another embodiment, the emulsifier(s) are selected from stearic acid, sodium dihydroxycetyl phosphate, glyceryl stearate, polysorbate 20, or mixtures thereof. When using stearic acid, it is preferred to combine it with triethanolamine (TEA).

The composition according to the invention also contain ingredients commonly used in the cosmetic industry, such as film formers, waxes, oils, thickening agents, suspending agents, plasticizers, solvents, colorants, fillers, emollients and preservatives. One or more emulsifiers are present in the non-aqueous compositions to improve the wear of the composition.

The compositions can be used for making-up the eyes, hair, lips, and/or skin, by applying the compositions of the present invention to the appropriate surface. Invention compositions in the form of mascara produce increased stability and better adherence to keratin fibres and provide long wear, greater wear resistance, improved water resistance, and improved cosmetic properties. Lotions employing the composition of the invention provide increased transfer resistance and water resistance and greater wearability. Eyeliner employing the composition of the invention produces increased stability and better adherence to eyelid tissue, and also provides greater water resistance and improved cosmetic properties Emulsifiers The compositions according to the invention comprises one or more emulsifiers preferably in a proportion that provides an ability of the non-aqueous composition to stay on an applied surface for longer periods of time, relative to similar or the same compositions that do not contain an emulsifier. This amount includes, for example, those amounts discussed above and amount preferably ranging from 0.2 to 10% by weight, relative to the total weight of the composition, and better still from 0.5% to 5% by weight. Suitable surfactants are discussed above, and others are found in the "Encyclopedia of Chemical Technology, Kirk-Othmer", Volume 22, pp. 333-432, 3rd Edition, 1979, Wiley, and in particular pp. 347-377 of this reference, which is hereby specifically incorporated by reference.

In addition to the above description of useful emulsifiers, the following is provided. Emulsifiers useful herein include anionic, nonionic, amphoteric and/or zwitterionic surfactants. In a preferred embodiment the surfactants are characterized by fatty acids, salts of phosphate esters of alcohols, glyceryl esters, ethoxylated surfactants, or mixtures thereof. In another embodiment, the emulsifier(s) are selected from stearic acid $[CH_3(CH_2)_{16}COOH]$, potassium and sodium dihydroxycetyl phosphate [sodium salt of a complex mixture of phosphate esters of dihydroxycetyl alcohol], glyceryl stearate $[CH_3(CH_2)_{16}COOCH_2CHOHCH_2OH]$, polysorbate 20, or mixtures thereof. When using stearic acid, it is preferred to combine it with triethanolamine (TEA).

Anionic surfactants may be employed alone or in admixture, and include, but are not limited to, alkaline salts, ammonium salts, amine salts or amino-alcohol salts of the following compounds: phosphate esters of alcohols, alkylphosphates/alkylether phosphates, alkyl sulfates, alkyl ether sulfates, alkylamide sulfates, ether sulfates, alkylarylpolyether sulfates and monoglyceride sulfates, alkylsulfonates, alkylamide sulfonates, alkylaryl sulfonates, alpha-olefin sulfonates and paraffin sulfonates, alkylsulfosuccinates, alkylether sulfosuccinates and alkylamide sulfosuccinates, alkylsulfosuccinamates, alkylsulfoacetates and alkylpolyglycerol carboxylates, alkylsarcosinates, allylpolypeptidates, alkylamidopolypeptidates, alkylisethionates and alkyltaurates, or mixtures thereof. The term "alkyl" used above means a hydrocarbon chain having generally from 12 to 18 carbon atoms.

Anionic surfactants also include fatty acid salts, such as those of oleic, ricinoleic, palmitic and stearic acid, copra oil or hydrogenated copra oil acids, and in particular, amine salts such as amine stearates.

Anionic surfactants also include acyl lactylates, the acyl radical of which contains 8 to 20 carbon atoms, and polyglycolic ether carboxylic acids having the formula $R_4(OCH_2CH_2)n\text{-}OCH_2COOH$, wherein $R_4$ represents a linear alkyl having 12 to 18 carbon atoms and "n" is a whole number between 5 and 15, and the salts of said acids; and $C_{16}$-$C_{30}$ fatty acids neutralized with amines, ammonia or alkaline salts.

Nonionic surfactants, which may be utilized alone or in admixture, include, but are not limited to, glyceryl esters, such as gylceryl stearate; ethoxylated surfactants, such as Polysorbate-20 and related sorbitan derivatives; Laureth-7, Laureth-4, Sepigel® 305 available from SEPPIC, and other similar ingredients; alcohols; alkylphenols; polyethoxylated; polypropoxylated or polyglycerolated fatty acids; fatty acids, such as stearic acid; fatty alcohols, polyethoxylated or polyglycerolated fatty alcohol, such as, polyethoxylated stearyl alcohol or polyethoxylated cetylstearyl alcohols; fatty acid esters of sucrose and alkylglucose esters, in particular polyoxyethylenated fatty esters of $(C_1\text{-}C_6)$ alkylglucose.

Emulsifiers also include copolymers of ethylene and propylene oxides, condensates of ethylene and propylene oxides on fatty alcohols, polyethoxylated fatty amides, polyethoxylated fatty amines, ethanolamides fatty acid esters of glycol, fatty acid esters of oxyethylene or non-oxyethylene sorbitan, fatty acid esters of saccharose, fatty acid esters of polyethylene glycols, phosphoric triesters and fatty acid ester derivatives of glucose.

Emulsifiers further include condensation products of a monoalcohol, an alpha-diol, an alkylphenol, an amide or a diglycolamide with glycidol or a glycidol precursor, such as, described in French patent, FR 71.17206 (2.091.516), having the formula $R_5CHOHCH_2O\text{—}(CH_2CHOHCH_2O)pH$, wherein $R_5$ represents an aliphatic, cycloaliphatic or arylaliphatic radical having, preferably, between 7 and 21 carbon atoms, the aliphatic chains optionally containing ether, thioether or hydroxymethylene groups, and "p" is a whole number between 1 and 10. Further mention can be made of compounds, described in French patent 1.477.048, having the formula: $R_6OC_2H_3O(CH_2OH)qH$, wherein $R_6$ represents an alkyl, alkenyl or alkylaryl radical and "q" has a statistical value between 1 and 10. Mention can also be made of compounds described in French patent, FR 76.31975 (2.328.763) having the formula: $R_7CONHCH_2CH_2\text{—}OCH_2CH_2\text{—}O\text{—}(CH_2CHOHCH_2O)rH$, wherein $R_7$ represents a linear or branched, saturated or unsaturated, aliphatic, optionally containing one or several hydroxyl groups said aliphatic having between 8 and 30 carbon atoms, of natural or synthetic origin, and "r" is a, whole or decimal number between 1 and 5, and designates the average condensation degree. There can be employed, as the nonionic surface active agent, a mixture of oil(s) and/or fatty alcohols or even polyethoxylated or polyglycerolated alcohols, such as polyethoxyl stearyl or cetylstearyl alcohols.

The composition may comprise one or more silicone surfactants, including, but not limited to, alkyl or alkyloxydimethicone copolyols. Suitable silicones are described, for example, in U.S. Pat. No. 4,311,695, which is hereby specifically incorporated by reference. The silicones sold by the company Dow Corning under the trade name Q2-5220 and by the company Rhone Poulenc under the name MIRASIL DMCO may also be used.

The compositions of the invention may also comprise organosilicone emulsifiers. Examples of organosilicone emulsifiers include cetyl dimethicone copolyol-polyglyceryl-4-isostearate-hexylaurate (ABIL® WE 09) available from Goldschmidt Chemical Corporation; Cetyl Dimethicone Copolyol (ABIL® EM 90), (ABIL® EM 97), Laurylmethicone Copolyol (5200), Cyclomethicone (and) Dimethicone Copolyol (DC 5225 C and DC 3225 C), available from GE Silicones; Cyclopentasiloxane & Dimethicone Copolyol (GE SF 1528).

Film Formers

The compositions of the invention may contain one or a mixture of two or more film-forming agents, or film formers. The use of a film-former improves the wear of the composition, and can confer transfer-resistance to the makeup product. The film-forming agent may be any compound/composition which is cosmetically acceptable for use. Examples of useful film-forming agents include, but are not limited to, styrene block copolymers, such as the Versagel copolymers, alkyl acrylate copolymers (ULTRASOL), polyisobutene, polyamide resins, natural waxes, polymers such as polyethylene polymers, and copolymers of PVP, ethylene vinyl acetate, dimethicone gum, and resins, such as shellac, polyterpenes, and various silicone resins, e.g., trimethylsiloxysilicate. The film-former is used in an amount of from about 0.1-50%, more preferably from about 1-20%.

Preferred polyamides include the commercial products sold by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of at least one polyamide polymer that may be used in the composition according to the present invention include polyamide polymers resulting from the condensation of at least one aliphatic dicarboxylic acid and at least one diamine, the carbonyl and amine groups being condensed via an amide bond. Examples of these polyamide polymers are those sold under the brand name Versamid by the companies General Mills Inc. and Henkel Corp. (Versamid 930, 744 or 1655) or by the company Olin Mathieson Chemical Corp. under the brand name Omamid, in particular Omamid S or C. These resins have a weight-average molecular mass ranging from 6000 to 9000. For further information regarding these polyamides, reference may be made to U.S. Pat. Nos. 3,645,705 and 3,148,125.

Other examples of polyamides include those sold by the company Arizona Chemicals under the references Uni-Rez (2658, 2931, 2970, 2621, 2613, 2624, 2665, 1554, 2623 and 2662) and the product sold under the reference Macromelt 6212 by the company Henkel. For further information regarding these polyamides, reference may be made to U.S. Pat. No. 5,500,209. Such polyamides display high melt viscosity characteristics. MACROMELT 6212, for example, has a high melt viscosity at 190° C. of 30-40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins disclosed in U.S. Pat. Nos. 5,783,657 and 5,998,570.

Other film formers include those organosiloxane resins described in US2003/0039620, incorporated herein by reference, and particularly the "MQ" resins as described in U.S. Pat. No. 5,330,747 (Krzysik), and the "MK" resins as described in US 2002/0031488, both incorporated herein by reference. Other useful silicone resins are described in US2002/0114773, U.S. Pat. Nos. 5,676,938, 5,589,165, 6,589,517 and 5,015,469, all incorporated herein by reference. Still other film formers include block copolymers comprising a styrene/butylene/ethylene/styrene copolymer (tri-block), an ethylene/propylene/styrene copolymer (radial or star block) or a mixture or blend of the two. (Some manufacturers refer to block copolymers as hydrogenated block copolymers, e.g. hydrogenated styrene/butylene/ethylene/styrene copolymer (tri-block) or hydrogenated ethylene/propylene/styrene copolymer (radial or star block), all of which are within the scope of the invention.). Specific examples include Versagel MD870, Versagel M5960, or Versagel M5970, all of which are available from Penreco of Houston Tex., and block copolymers available from Brooks Industries, such as Gel Base.

Film formers include di-block, tri-block, multi-block and/or radial or star block copolymer film formers, containing at least two thermodynamically incompatible segments. A di-block is usually defined as A-B type or a hard segment (A) followed by a soft segment (B) in sequence. A tri-block is usually defined as an A-B-A type copolymer or a ratio of one hard, one soft, and one hard segment. Multiblock or radial or star copolymer film formers usually contain any combination of hard and soft segments, provided that there are both hard and soft characteristics. An example of a hard block copolymer segment is styrene, while examples of soft block copolymer segments are ethylene, propylene, and butylene or combinations thereof.

Film formers include Kraton® rubbers (Shell Chemical Company). Kraton® rubbers are thermoplastic elastomers in which the polymer chains comprise a tri-block, di-block, or radial or star block configuration, or numerous mixtures thereof. The Kraton® tri block rubbers have polystyrene segments on each end of a rubber segment, while the Kraton® di-block rubbers have a polystyrene segment attached to a rubber segment. The Kraton® radial or star configuration, in a further preferred embodiment, may be a four-point or other multipoint star made of rubber with a polystyrene segment attached to each end of a rubber segment. The configuration of each of the Kraton® rubbers form separate polystyrene and rubber domains.

Each molecule of Kraton® rubber is said to comprise block segments of styrene monomer units and rubber monomer and/or co-monomer units. The most common structure for the Kraton® triblock copolymer is the linear A-B-A block type styrene-butadiene-styrene, styrene-isoprene-styrene, or styrene-ethylenebutylene-styrene. The Kraton® di-block is preferably the AB block type such as styrene-ethylenepropylene, styrene-ethylenebutylene, styrene-butadiene, or styrene-isoprene. The Kraton® rubber configuration is well known in the art, and any block copolymer film former with a similar configuration is within the practice of the invention.

The block copolymer film former may preferably be formulated by dissolving the block copolymer in a hydrocarbon solvent. Hydrocarbons useful in the practice of the invention include, but are not limited to, mineral oils, mineral solvents, mineral spirits, petroleum, waxes, synthetic hydrocarbons, animal oils, vegetable oils, and mixtures of various hydrogen carbons. In a preferred embodiment, the block copolymer film former is formulated by dissolving the block copolymer in isododecane or a light paraffinic solvent. In another preferred embodiment, the block copolymer film former may be formulated by dissolving the block copolymer in a non-hydrocarbon solvent such as amyl acetate, butyl acetate, isobutyl acetate, ethyl acetate, propyl acetate or isopropyl acetate.

The solvent and solubility conditions for formulating a block copolymer film former from a block copolymer will be chosen by a person skilled in the art, in order to prepare a composition which has the desired properties. One of ordinary skill in the art will be able to determine the solubility parameters, and choose a solvent based on the block copolymer chosen for the envisaged application. More information regarding solubility parameters and solvents useful in the processing of specific block copolymers is available from the various manufacturers of block copolymers, e.g. Shell Chemical Company. Additional discussions of polymer solubility parameter concepts are presented in: Encyclopedia of Polymer Science and Technology, Vol. 3, Interscience, New York (1965) and Encyclopedia of Chemical Technology, Supp. Vol., Interscience, New York (1971), the disclosures of which are hereby incorporated by reference.

Preferably, the block copolymer film formers offer excellent adherence to the skin, and are tack free. It is preferred that the copolymer film former be present in the outer phase of any cosmetic formulation and at high concentrations. Additionally, it is preferred that the copolymer film former be compatible with the other raw materials of that phase.

Depending on the application, the concentration of block copolymer film former may vary considerably. One of skill in the art will be able to determine routinely the preferred concentration of block copolymer film former depending on the application and the transfer resistance properties desired. For example, for cosmetic foundations, the block copolymer film former or block copolymer film former mixtures may preferably be used in an amount from less than about 1% to about 30% by weight, and more preferably from about 1% to about 15% by weight. For eyeliner formulations, the block copolymer film former or block copolymer film former mixture preferably may vary from about 5% to about 70% by weight, and more preferably from about 20% to about 70% by weight. For lipstick formulations, the block copolymer film former or block copolymer film former mixture preferably may vary from about 1% to about 70% by weight, and more preferably from about 10% to about 70% by weight.

The block copolymer film former may be combined in a formulation with an additional film former (b). This additional film former may improve smoothness or spreadability, water-resistance, transfer resistance properties, or other cosmetic or pharmaceutical properties desired by one of skill in the art.

The preferred concentration of additional film formers may also be determined by one of skill in the art and can vary considerably based on the application. For example, for cosmetic emulsions, an additional film former or combination of additional film formers is preferably used in an amount from less than 1% to 15% by weight, and more preferably from 1% to 10% by weight. For eyeliner formulations, the additional film former or combination of additional film formers are preferably used in an amount from less than 0.5% to 15% by weight, more preferably from 1% to 10% by weight. For lipstick formulations, the additional film former or combination of additional film formers is preferably used in an amount from less than 0.5% to 15% by weight, more preferably from 1% to 10% by weight.

Examples of additional film formers include: vinylpyrrolidone/vinyl acetate (PVP/VA) copolymers such as the Luviskol VA grades (all ranges) from BASF® Corporation, and the PVP/VA series from ISP; acrylic fluorinated emulsion film formers, including Foraperle® film formers, such as Foraperle® 303 D from Elf Atochem; GANEX® copolymers, such as Butylated PVP, PVP/Hexadecene copolymer, PVP/Eicosene copolymer or tricontanyl; Poly (vinylpyrrolidone/diethylaminoethyl methacrylate) or PVP/Dimethylaminoethylmethacrylate copolymers such as Copolymer 845; Resin ACO-5014 (Imidized IB/MA copolymer); other PVP based polymers and copolymers. Film formers also include silicone gums; cyclomethicone and dimethicone crosspolymers (For example, Dow Corning® 2-9040, See U.S. Pat. No. 5,654,362, the disclosure of which is hereby incorporated by reference); trimethyl siloxysilicate, such as SR 1000, SS4230, or SS4267 available from GE Silicones; alkyl cycloalkylacrylate copolymers (See WO98/42298 the disclosure of which is hereby incorporated by reference); or Mexomere® film formers and other allyl stearate/vinyl acetate copolymers (allyl stearate/VA copolymers). Film formers also include polyolprepolymers such as PPG-12/SMDI copolymer, polyolprepolymers such as PPG-12/SMDI copolymer, poly(oxy-1,2-ethanediyl), alpha-hydro-omega-hydroxy-polymer with 1,1'-methylene-bis-(4-isocyanatocyclohexane) available from Barnet; Avalure™ AC Polymers (Acrylates Copolymer) and Avalure™ UR polymers (Polyurethane Dispersions), available from BFGoodrich.

Additional film formers include any film former prepared from chemistry known in the art, such as: PVP, acrylates, and urethanes; synthetic polymers of the polycondensate type or free-radical type, or ionic type; polymers of natural origin; and mixtures thereof or any other film formers known within the practice of the cosmetic and pharmaceutical arts which one skilled in the art may determine to be compatible.

Waxes

The compositions according to the invention may also contain one or a mixture of two or more waxes. Waxes include waxes of animal origin, waxes of plant origin, waxes of mineral origin, synthetic waxes, and various fractions of waxes of natural origin. The waxes can be present in an amount ranging from 5% to 50% by weight, relative to the total weight of the composition.

Animal waxes include, but are not limited to, beeswax, spermaceti, lanolin wax, derivatives of lanoline and China insect waxes. Vegetable waxes include, but are not limited to, rice wax, carnauba wax, candelilla wax, ouricurry wax, cork fiber wax, sugar cane wax, cocoa butter, Japan wax and sumac wax. Mineral waxes include, but are not limited to, montan wax, microcrystalline waxes, paraffins, ozokerite, petroleum jelly and ceresine. Synthetic waxes include, but are not limited to, polyethylene homopolymer and copolymer waxes, synthetic beeswax, waxes obtained by the Fisher and Tropsch synthesis, and silicon waxes.

Waxes obtained by catalytic hydrogenation of animal or vegetable oils, having linear or branched $C_8$-$C_{32}$ fatty chains are also used, as well as fatty esters and glycerides.

Waxes also include silicone waxes, among which, mention may be made of polymethylsiloxane alkyls, alkoxys and/or esters. The waxes may be in the form of stable dispersions of colloidal wax particles, in accordance with known methods, such as, "Microemulsions Theory and Practice", L. M. Prince Ed., Academic Press (1977), pages 21-32. Lignate wax may also be used.

Waxes useful in the present compositions may provide one or more of the following properties, including, but not limited to, bulking, texture, and a degree of water resistance. The waxes should not substantially reduce the gloss properties of a glossy film former.

Oils

The compositions according to the invention may also comprise one or more oils, including, but not limited to, oils that are mineral, animal, vegetable or synthetic in nature. The oils may be volatile or non-volatile at ambient temperature.

Oils of mineral origin include, but are not limited to, liquid paraffin and liquid petroleum. Oils of animal origin include, but are not limited to, squalane or perhydrosqualene. Oils of vegetable origin include, but are not limited to, sweet almond oil, calophyllum oil, palm oil, avocado oil, jojoba oil, sesame oil, olive oil, castor oil, and cereal germ oils, such as, wheat germ oil.

Synthetic oils include, but are not limited to, esters of the formula, $R_1COOR_2$, in which: $R_1$ is the residue of a higher fatty acid having 7 to 20 carbon atoms and $R_2$ is a hydrocarbon radical having 3 to 30 carbon atoms. These esters include, but are not limited to, purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate, and esters derived from lanolic acid, such as isopropyl lanolate and isocetyl lanolate.

Other synthetic oils include, but are not limited to, isoparaffins; isododecane; isohexadecane; polyisobutenes and hydrogenated polyisobutene; acetylglycerides; and octanoates and decanoates of polyalcohols, such as, those of glycol and of glycerol; the ricinoleates of alcohols and of polyalcohols, such as, that of cetyl alcohol, propylene glycol dicaprylate and diisopropyl adipate; fatty alcohols, such as, oleyl alcohol, linoleyl alcohol, linolenyl alcohol, isostearyl alcohol and octyldodecanol.

Additional synthetic oils include, but are not limited to, silicone oils, such as, optionally functionalized linear polydiorganosiloxanes; cyclic polydiorganosiloxanes, and in particular, cyclotetradimethicones and cyclopentadimethicones; and organopolysiloxanes, such as, alkyl-, alkoxy- or phenyldimethicones, and especially phenyltrimethicone; non-volatile fluorinated oils, such as, perfluorodecalin, perfluorophenanthrene, perfluoroalkanes, perfluoropolyethers and perfluoropolyesters; and partially fluorinated hydrocarbon oils.

Oils also include hydrocarbon oils, such as, liquid paraffin or liquid petrolatum; perhydrosqualene; arara oil; sweet almond oil; calophyllum oil; palm oil; castor oil; avocado oil; jojoba oil; olive oil or cereal germ oil; esters of lanolic acid, of oleic acid, of lauric acid or of stearic acid; alcohols, such as, oleyl alcohol, linoleyl alcohol or linolenyl alcohol, isostearyl alcohol or octyldodecanol. Mention may also be made of silicone oils such as PDMSs, which are optionally phenylated, such as, phenyltrimethicones. It is also possible to use volatile oils, such as, cyclotetradimethylsiloxane, cyclopentadimethylsiloxane, cyclohexadimethylsiloxane, methylhexyldimethylsiloxane or isoparaffins.

The expression "hydrocarbon-based oil" means oil mainly containing hydrogen and carbon atoms and possibly oxygen, nitrogen, sulphur, or phosphorus atoms. Examples of volatile hydrocarbon-based oils, which are suitable for the compositions of the invention, include hydrocarbon-based oils containing from 8 to 16 carbon atoms, such as, $C_8$-$C_{16}$ isoalkanes (or isoparaffins) and $C_8$-$C_{16}$ branched esters, such as, isododecane (also known as 2,2,4,4,6-pentamethylheptane), isodecane, isohexadecane, and isohexyl neopentanoate, and mixtures thereof. Other volatile hydrocarbon-based oils, such as, petroleum distillates, including those sold under the name SHELL SOLT by Shell, can also be used.

Additional hydrocarbon oils include, but are not limited to, mink oil, turtle oil, soya oil, grape seed oil, sesame oil, corn oil, rapeseed oil, sunflower oil, cotton oil, fatty esters, such as, isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl or linolenyl alcohol, isostearyl alcohol or octyldodecanol; silicone oils such as PDMSs, which are optionally fluorinated, or substituted with functional groups such as hydroxyl, thiol and/or amine groups; polysiloxanes modified with fatty acids, with fatty alcohols or with polyoxyalkylenes, fluoro silicones and perfluoro oils. Volatile oils such as cyclotetradimethylsiloxane, cyclopentadimethylsiloxane, cyclohexadimethylsiloxane and methylhexyldimethylsiloxane or isoparaffins, such as, "ISOPARs", in particular isododecane.

Volatile oils include, but are not limited to, volatile silicones such as, cyclic and volatile silicone oils, such as, octamethylcyclotetrasiloxane, decamethylcyclopentasiloxane, docadecamethylcyclohexasiloxane; volatile linear silicones, such as, octamethyltrisiloxane, heptamethylhexyltrisiloxane, heptamethyloctyltrisiloxane, and decamethyltetrasiloxane; or alternatively, volatile fluoro oils, such as, nonafluoromethoxybutane or perfluoromethylcyclopentane.

Fluoro oils may also be used, including, but not limited to, fluorosilicone oils, polyfluoro ethers, and fluorosilicones.

Thickening Agents

One or more thickening agents may be used in the compositions of the present invention, including, but not limited to, waxes, silica gel, gums, clays, fumed silica, fatty acid soaps, and various hydrocarbon gels. Thickening agents of natural origin include various gums, such as, arabic, guar and carob gums. Thickening agents of synthetic origin include water-soluble cellulosic derivatives, cellulose ether derivatives possessing quaternary ammonium groups, starch derivatives, cationic polysaccharides, acrylic or methacrylic polymer salts, polyenes, polyisobutene, hydrogenated polyisobutene and polysiloxanes. Water-soluble cellulosic derivative may include methylcelluloses, hydroxyethylcelluloses, hydroxylpropylmethylcelluloses, carboxymethylcelluloses and their mixtures.

Thickening agents for mascara compositions may comprise a mixture of a polyethylene glycol and polyethylene glycol stearate and/or distearate, or a mixture of phosphoric esters and fatty amides.

Thickeners that do not substantially reduce the gloss properties of a glossy film former include organic thickeners and inorganic thickeners. Suitable organic thickeners include, but are not limited to, PEG-8 dioleate, available from Lipo, as LIPOPEG® 4-DO; polyglyceryl-2 diisostearate, available from Alzo as DERMOL® DGDIS; nonionic associative polymers, such as, PEG-150/decyl/SMDI copolymer and PEG-150/stearyl/SMDI copolymer, available from ISP as Aculyn 44® and Aculyn 46®, respectively; nonionic non-associative polymers; anionic associative polymers, such as, acrylates/steareth-20 methacrylate copolymer, available from ISP as Aculyn 22®; and anionic non-associative polymers, such as, acrylates copolymer, available from ISP as Aculyn 33® Suitable inorganic thickeners include, but are not limited to, Laponite® XLG (Na Mg silicate) and MSS 500/N (silica). The thickener may also be a mixture of thickeners, such as, a mixture of associative and nonassociative polymers.

In addition, the composition may comprise at least one thickener, preferably of hydrophilic nature. These thickeners include carboxyvinyl polymers (carbomer); acrylic copolymers, such as, acrylate/alkylacrylate copolymers; polyacrylamides, polysaccharides; natural gums and clays.

Suspending Agents

The compositions of the invention may include one or more suspending agents, including but not limited to, quaternary ammonium compounds, such as, Quaternium—18 Hectorite (Bentone 38).

Plasticizing Agents

A plasticizing agent may be employed in the compositions of the invention, so as to improve cosmetic and mechanical properties, such as, flexibility, of the resulting formulation. The plasticizing agent may be added in an amount between 5 and 90 percent, and preferably, between 10 and 80 percent, by weight, relative to the weight of the composition.

Plasticizers are materials which soften synthetic polymers. They are frequently required to avoid brittleness and cracking of film formers. One skilled in the art may routinely vary the amount of plasticizer desired, based on the properties desired and the application envisaged. Plasticizers include propylene carbonate, lecithin, polysorbates, dimethicone copolyol, glycols, citrate esters, glycerin, dimethicone, and other similar ingredients disclosed in the International Cosmetic Dictionary and Handbook Vol. 2 (7.sup.th ed. 1997); more particularly, the plasticizers disclosed on page 1654. The disclosure of the International Cosmetic Dictionary and Handbook Vol. 2, page 1654, is hereby incorporated by reference.

The plasticizing agent may be of the hydrophilic or hydrophobic type, and is preferably introduced in admixture with the organic solvent during the preparation, or after the preparation, of the composition.

Common plasticizers include, but are not limited to, glycols and their derivatives, such as, diethylene glycol ethyl ether, diethylene glycol methyl ether, diethylene glycol butyl ether, diethylene glycol hexyl ether, ethylene glycol ethyl ether, ethylene glycol butyl ether or ethylene glycol hexyl ether, glycerol esters, propylene glycol derivatives, and in particular, propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether, propylene glycol butyl ether; acid esters, in particular, carboxylic acid esters, such as citrates, phthalates, adipates, carbonates, tartrates, phosphates and sebacates; oxyethylenated derivatives such as oxyethylenated oils, in particular, plant oils such as castor oil; silicone oils.

Solvents

The compositions of the invention may include one or more solvents, including, but not limited to, isododecane, acetone, methylethylketone, tetrahydrofuran, 1,2-dichloroethane, methyl acetate, ethyl acetate, isopropanol and ethanol.

Colorants

The compositions according to the present invention may contain one or more colorants, such as pigments and/or dyes. The pigments of the compositions may be inorganic or organic. These pigments include, but are not limited to, iron oxides, titanium dioxide, zinc oxide, D&C Red No. 36 and D&C Orange No. 17, calcium lakes of D&C Red No. 7, 11, 31 and 34, barium lake of D&C Red No. 12, D&C Red No. 13 strontium lake, aluminium lakes of FD&C Yellow No. 5, of FD&C Yellow No. 6, of D&C Red No. 27, of D&C Red No.

21 and of FD&C Blue No. 1, manganese violet, chromium oxide, chromium oxide, ferric blue, cerium oxide, and ultramarine blue.

The proportion of pigments, in the mascara compositions according to the invention, is generally between 0.1 and 25 weight percent, relative to the total weight of the composition, according to the coloration and intensity of the sought after coloration. However, the amount of pigment may vary depending on the application envisaged. It has been found that increased amounts of pigment may result in a matte effect.

The inorganic pigments include, but are not limited to, titanium dioxide, which may be optionally surface-treated; zirconium oxide or cerium oxide; as; iron oxide or chromium oxide; manganese violet; ultramarine blue; chromium hydrate and ferric blue. The organic pigments include, but are not limited to, carbon black, pigments of D & C type, and lakes based on cochineal carmine, barium, strontium, calcium or aluminium.

The compositions may also contain pearlescent pigments including, but not limited to, white pearlescent pigments, such as, mica coated with titanium, or with bismuth oxychloride; colored pearlescent pigments, such as, titanium mica with iron oxides; titanium mica with, in particular, ferric blue or chromium oxide; titanium mica with an organic pigment of the abovementioned type and pearlescent pigments based on bismuth oxychloride.

The dyes include, but are not limited to, eosine derivatives, such as D&C Red No. 21, and halogenated fluorescein derivatives, such as D&C Red No. 27, D&C Orange No. 5, in combination with D&C No. 21 and D&C Orange No. 10. Depending on the composition, the dyes may be in particle form, or may be in a form in which they are solubilized in the vehicle of the composition.

Fillers

The present compositions may include one or more fillers. The fillers include those of natural or synthetic origin. Fillers include, but are not limited to, mineral powders, such as, talc, kaolin, mica, silica, silicates, alumina, zeolites, hydroxyapatite, sericite, titanium micas, barium sulphate, bismuth oxychloride, boron nitride; metal powders, such as, aluminum powder, vegetable powders, such as starch, maize, wheat or rice powders; and organic powders, such as, nylon, polyamide, polyester, polytetrafluoroethylene or polyethylene powders.

The various powders may be coated, for example with metal salts of fatty acids, amino acids, lecithin, collagen, silicone compounds, fluorinated compounds, or with any other Customary coating.

The fillers may generally be present in a maximum proportion of approximately 98%, by weight, relative to the total weight of the composition.

Fillers also include talc, mica, silica, kaolin, nylon powder, poly-beta-alanine powder and polyethylene powder, Teflon, lauroyllysine, starch, boron nitride, tetrafluoroethylene polymer powders, hollow microspheres such as Expancel (Nobel is Industrie), polytrap (Dow Corning) and silicone resin microbeads (Tospearls from Toshiba for example), precipitated calcium carbonate, magnesium carbonate and hydrocarbonate, hydroxyapatite, hollow silica microspheres (Silica Beads from Maprecos), glass or ceramic microcapsules. Mention may also be made of metal soaps derived from organic carboxylic acids having from 8 to 22 carbon atoms, preferably from 12 to 18 carbon atoms, for example zinc, magnesium or lithium stearate, zinc laurate and magnesium myristate.

The fillers may be chosen from those that are well-known to those skilled in the art, and that are commonly used in cosmetic compositions. Fillers include zinc oxide and titanium oxide, which are generally used in the form of particles, not exceeding a few microns in size; calcium carbonate; magnesium carbonate or magnesium hydrocarbonate; microcrystalline cellulose; silica; synthetic polymer powders such as polyethylene, polyesters (polyethylene isophthalate or terephthalate); and polyamides.

Fillers and mothers-of-pearl may be added to the formulations to modify the texture of the composition and the matteness/gloss effect. Fillers should be understood to mean lamellar or non-lamellar, inorganic or synthetic, colorless or white particles. Mothers-of-pearl should be understood to mean irridescent particles produced especially by certain mollusks in their shell, or else synthesized. Pearling agents that may be used include mica, iron oxides, titanium dioxide and any other pearling agent known in the cosmetic arts.

Emollients

Emollients may also be used in the compositions of the invention. Emollients include, but are not limited to, hydrogenated polyisobutene, glycerin, propylene glycol, cyclomethicone, dimethicone, and emollients and other similar ingredients disclosed in the International Cosmetic Dictionary and Handbook Vol. 2 (7.sup.th ed. 1997); more particularly the emollients disclosed on pages 1656-1661. The disclosure of the International Cosmetic Dictionary and Handbook Vol. 2, pages 1656-1661, is hereby incorporated by reference.

Preserving Agents

The compositions may contain one or more preservatives, such as, phenoxyethanol, methyl paraben, butyl paraben, propyl paraben, sulfuric acid, benzoic acid, imidazolidinyl urea and other conventional preservatives.

Additional Formulation Agents

The composition may also comprise any other additive usually used in such compositions, including, but not limited to, dispersion enhancing agents; oily gelling agents; humectants; softners, UV-screening agents; antioxidants, fragrances; antifoaming agents; wetting agents; chelators; preserving agents; cosmetic active agents; water-proofing additives; moisturizers; vitamins; vitamin derivatives; conditioning agents, such as Lexorez 200; botanical extracts, pharmaceutical active agents; moisturizers, binders, essential fatty acids, sphingo lipids, sunscreens, film formers, liposoluble polymers such as polyalkylenes, in particular polybutene, polyacrylates and silicone polymers which are compatible with fatty substances.

A person skilled in the art will take care to select these possible additional compounds, and/or the amount thereof, such that the advantageous properties of the composition, according to the invention, are not, or are substantially not, adversely affected by the addition envisaged. These substances may be selected variously by the person skilled in the art, in order to prepare a composition which has the desired properties, for example, consistency or texture.

When the application envisaged for the composition is an application as a mascara, the composition according to the present invention may be in the form of a suspension, a solution or a microdispersion of waxes in a non-aqueous solvent, non-aqueous solid or non-aqueous pasty form, or alternatively, in the form of an oily gel.

In another embodiment of the invention, the compositions may be in the form of a cast product, and comprise at least one wax, and a dispersion of crosslinked and surface-stabilized polymer particles in a cosmetically, dermatologically, hygienically or pharmaceutically acceptable liquid fatty substance. The compositions may then be in the form of a stick or pencil, or in the form of a flexible paste. They may be in the form of a cast product, prepared in a manner which is common to those skilled in the art, or alternatively, in the form of a cupel which can be used by direct contact or with a sponge. Cast products may include cast foundation, cast make-up rouge, eyeshadow, lipstick, a care base for the lips, or a care balm.

When it is in the form of a powder, in particular a compacted powder, the composition may be prepared by a person skilled in the art, in the usual manner, and in particular, by mixing the various constituents and compacting using a mechanical press. The composition thus obtained has the appearance of a compacted powder, for example, in a cupel, stick or cylinder form, or in any other complex form. The composition according to the invention may be in the form of a pharmaceutical or hygiene composition, such as, a body powder, a baby powder or an antiperspirant powder. It may also be in the form of a make-up product, such as, a make-up rouge or an eyeshadow, a blusher or a face powder.

The compositions of the invention may also be in the form of oily gel, oily liquid or oil, paste, stick or aerosol, or alternatively, in the form of a vesicle dispersion containing ionic and/or nonionic lipids. These pharmaceutical forms are prepared according to the usual methods of the fields considered. These compositions for topical application may constitute a cosmetic, dermatological, hygiene or pharmaceutical composition for protection, treatment or care of the face, the neck, the hands or the body (for example an anhydrous care cream, a sun oil or a body gel), a make-up composition (for example a make-up gel) or an artificial tanning composition.

The composition according to the invention can be prepared according to the usual methods of the fields under consideration.

Having generally described this invention, a further understanding can be obtained by reference to certain specific examples which are provided herein for purposes of illustration only, and are not intended to be limiting, unless otherwise specified.

EXAMPLES

Compositions were prepared according to the following general procedures:
1. In the main beaker, weigh out phase A and mix on the homogenizer for 60 minutes at room temperature.
2. Once the batch has been mixing for 60 minutes, slowly add half of phase B to the main beaker. Begin heating to 70° C.
3. In a separate beaker combine phase C and heat to 85-90° C. with propeller mixing.
4. Once phase A and phase C have reached their optimal temperatures, add phase C to phase A. Allow batch to homogenize for 5 minutes while maintaining heat at 80-85° C.
5. Add the remainder of phase B to main beaker and continue homogenizing for 30 minutes while maintaining temperature at 80-85° C.
6. After step 5 is completed, remove batch from the homogenizer and begin cooling to 60° C. using sweep mixing.
7. At 60° C., add phase D and continue mixing until 30-35° C.

The compositions prepared were tested in a Waterproof Study which was conducted as follows:

Place a measured amount of product onto a glass slide and allow it to dry in a room temperature (25° C.) chamber for 24 hours. Place slide in a beaker and immerse slide in a measured amount of water sufficient to cover slide. Place a stir bar in the middle of the slide and place on a stir plate. Allow the stir bar to turn at medium speed over slide for 2 hours. After 2 hours, determine if the stir bar has made a hole.

Evaluation—The quantitative measurement for this study is as follows:

0—A hole is created exposing the base of the glass slide causing the removal of the product.

1—A hole is created exposing more than half of the base on the glass slide with significant removal of the product.

2—A hole is created exposing half the base on the glass slide with removal of to the product.

3—A smaller hole is created exposing less than half the base on the glass slide with disturbance to the film.

4—Product has been removed from the glass slide without creating a hole.

5—There has not been a disturbance of the film on the glass slide.

TABLE 1

| Phase | INCI Name | % EX. 1 | % Ex. A | % Ex. 2 | % Ex. 3 | % Ex. 4 | % Ex. 5 | % Ex. 6 | % Ex. 7 |
|---|---|---|---|---|---|---|---|---|---|
| A | Isododecane | 51.33 | 32.19 | 31.19 | 30.89 | 31.90 | 31.69 | 30.19 | 30.99 |
|   | MK Resin | 7.00 | 8.00 | 8.00 | 8.00 | 8.00 | 8.00 | 8.00 | 8.00 |
|   | Versagel MD 870 | 5.00 | 15.00 | 15.00 | 15.00 | 15.00 | 15.00 | 15.00 | 15.00 |
|   | Quatemium-18 Hectorite | 2.00 | 5.50 | 5.50 | 5.50 | 5.50 | 5.50 | 5.50 | 5.50 |
|   | Black Iron Oxide | 5.00 | 6.00 | 6.00 | 6.00 | 6.00 | 6.00 | 6.00 | 6.00 |
| B | Propylene Carbonate | 0.66 | 1.80 | 1.80 | 1.80 | 1.80 | 1.80 | 1.80 | 1.80 |
|   | TEA | N/A | N/A | N/A | 0.30 | N/A | N/A | N/A | 0.20 |
| C | Paraffin | 3.00 | 3.00 | 3.00 | 3.00 | 3.00 | 3.00 | 3.00 | 3.00 |
|   | Carnuba Wax | 5.00 | 3.50 | 3.50 | 3.50 | 3.50 | 3.50 | 3.50 | 3.50 |
|   | Beeswax | 7.00 | 4.00 | 4.00 | 4.00 | 4.00 | 4.00 | 4.00 | 4.00 |
|   | Polyamide Resin | 5.00 | 6.00 | 6.00 | 6.00 | 6.00 | 6.00 | 6.00 | 6.00 |
|   | Synthetic Beeswax | 4.00 | 3.50 | 3.50 | 3.50 | 3.50 | 3.50 | 3.50 | 3.50 |
|   | Lexorez 200 | 3.00 | 3.00 | 3.00 | 3.00 | 3.00 | 3.00 | 3.00 | 3.00 |
|   | Hydrogenated Polyisobutene | 2.00 | N/A | N/A | N/A | N/A | N/A | N/A | N/A |
|   | Phenoxyethanol | 0.01 | 0.01 | 0.01 | 0.01 | 0.01 | 0.01 | 0.01 | 0.01 |
|   | Permethyl 108A (Polyisobutene) | N/A | 3.50 | 3.50 | 3.50 | 3.50 | 3.50 | 3.50 | 3.50 |

TABLE 1-continued

| Phase | INCI Name | % EX. 1 | % Ex. A | % Ex. 2 | % Ex. 3 | % Ex. 4 | % Ex. 5 | % Ex. 6 | % Ex. 7 |
|---|---|---|---|---|---|---|---|---|---|
| | Sodium Dihydroxycetyl Phosphate | N/A | N/A | 1.00 | N/A | N/A | N/A | 2.00 | 1.00 |
| | Stearic Acid | N/A | N/A | N/A | 0.50 | 0.50 | N/A | N/A | N/A |
| | Glyceryl Stearate | N/A | N/A | N/A | 0.50 | 0.50 | N/A | N/A | N/A |
| | Tween 20 | N/A | N/A | N/A | N/A | N/A | 0.5 | N/A | N/A |
| D | Ultrasol (Alkyl Acrylates Copolymer) | N/A | 5.00 | 5.00 | 5.00 | 5.00 | 5.00 | 5.00 | 5.00 |

TABLE 2

Emulsifier Study

| Batch Number | Emulsifier System | Bulk Result | Waterproof Study |
|---|---|---|---|
| Example 1 | N/A | Matte, dry, grainy consistency | 4 |
| Example A | N/A | Semi matte, slightly dry, grainy consistency | 4 |
| Example 2 | Sodium Dihydroxycetyl Phosphate | High gloss and smooth consistency | 5 |
| Example 3 | Stearic Acid, Glyceryl Stearate, Triethanolamine | Higher gloss, smoother consistency in comparison to original | 5 |
| Example 4 | Stearic Acid, Glyceryl Stearate, without Triethanolamine | Less shiny, slightly more viscous, consistency is less smooth in comparison to previous batch, still better than original batch | 5 |
| Example 5 | Tween 20 | Higher gloss in comparison to original batch, consistency has slightly improved | 5 |
| Example 6 | Increased Sodium Dihydroxycetyl Phosphate | High Gloss, very good consistency comparable to batch containing less of same emulsifier | 5 |
| Example 7 | Sodium Dihydroxycetyl Phosphate, Triethanolamine | Less glossy than previous batch, better than original batch without emulsifier | 5 |

The following embodiment is prepared:

| | |
|---|---|
| Propylene Carbonate | 1.8 |
| BHT | 0.00309 |
| Zinc Oxide | 0.02 |
| Iron Oxides | 6 |
| Isododecane | 47.012 |
| Acrylates/Ammonium Methyacrylate Copolymer | 4.88 |
| Isobutylparaben | 0.00051 |
| Tetradibutyl pentaerythrityl hydroxyhdrocinnamate | 0.018 |
| Polymethylsilsesquioxane | 8 |
| Disteardimonium Hectorite | 4 |
| Synthetic Beeswax | 1.497 |
| Water | 5 |
| Paraffin | 1.49991 |
| Beeswax | 2 |
| *Copernicia Cerifera* (Carnuba) Wax | 2 |
| Polyisobutene | 5 |
| Preservatives - parabens and phenoxyethanol | 0.01249 |
| Surfactants | 0.1 |
| Ethylenediamine/stearyl dimer dilinoleate copolymer | 5.982 |
| SEB copolymer | 1.8 |
| SEBS copolymer | 0.375 |

The present invention compositions may take any form. In a preferred embodiment the form is not an emulsion.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

What is claimed is:

1. A non-aqueous composition comprising:
   an emulsifier mixture, present in an amount ranging from 0.5% to 5% by weight, relative to the total weight of the composition, and
   at least one film former chosen from styrene block copolymers, alkyl acrylate copolymers, polyamide resins, and organosiloxane resins,
   wherein the emulsifier mixture comprises at least two emulsifiers chosen from polysorbate 20, stearic acid, glyceryl stearate, and sodium dihydroxycetyl phosphate.

2. The non-aqueous composition of claim 1, further comprising a wax.

3. The non-aqueous composition of claim 1, further comprising a thickening agent.

4. The non-aqueous composition of claim 1, further comprising a filler.

5. The non-aqueous composition of claim 1, further comprising a solvent.

6. The non-aqueous composition of claim 1, further comprising a colorant.

7. The non-aqueous composition of claim 2, wherein the wax is selected from paraffin, carnuba wax, beeswax, synthetic beeswax or mixtures thereof.

8. A method for preparing a non-aqueous composition, comprising adding an emulsifier mixture to a non-aqueous medium,
wherein the emulsifier mixture comprises at least two emulsifiers chosen from polysorbate 20, stearic acid, glyceryl stearate, and sodium dihydroxycetyl phosphate,
wherein the emulsifier mixture is present in an amount ranging from 0.5% to 5% by weight, relative to the total weight of the composition, and
wherein the non-aqueous composition further comprises at least one film former chosen from styrene block copolymers, alkyl acrylate copolymers, polyamide resins, and organosiloxane resins.

9. A mascara composition comprising the non-aqueous composition of claim 1.

10. An eyeliner composition comprising the non-aqueous composition of claim 1.

11. A method of making-up the eyes, hair, lips and/or skin comprising applying the non-aqueous composition of claim 1 to the eyes, hair, lips and/or skin.

* * * * *